United States Patent [19]

Muir et al.

[11] 4,021,305

[45] May 3, 1977

[54] STRING CULTURE INOCULUM

[75] Inventors: Robert D. Muir, Glenwood, Ill.; Vijay K. Sangar, Foster City, Calif.

[73] Assignee: G. D. Searle & Co., Chicago, Ill.

[22] Filed: May 19, 1976

[21] Appl. No.: 687,724

[52] U.S. Cl. ................................. 195/54; 195/100
[51] Int. Cl.² ..................... C12B 1/02; C12K 3/00
[58] Field of Search ...................... 195/54, 99-102

[56] References Cited

UNITED STATES PATENTS

| | | | |
|---|---|---|---|
| 3,102,082 | 8/1963 | Brewer | 195/54 X |
| 3,767,790 | 10/1973 | Guttag | 195/102 X |

*Primary Examiner*—Lionel M. Shapiro
*Attorney, Agent, or Firm*—John J. McDonnell

[57] ABSTRACT

The present invention is concerned with a string culture inoculum comprising a string having stabilized cells of one of

| | |
|---|---|
| *Salmonella typhimurium* | ATCC 6994 |
| *Klebsiella pneumoniae* | ATCC 10031 |
| *Enterobacter cloacae* | ATCC 11367 |
| *Escherichia coli* | ATCC 25922 |
| *Citrobacter freundii* | ATCC 6750 |
| *Proteus vulgaris* | ATCC 881 |
| *Pseudomonas aeruginosa* | ATCC 15442 |
| *Shigella sonnei* | ATCC 11060 |
| *Serratia marcescens* | ATCC 14756 |
| *Staphylococcus aureus* | ATCC 25923 |
| *Staphylococcus epidermidis* | ATCC 17917 |
| *Streptococcus faicalis* | ATCC 10541 |
| *Streptococcus pyogenes* | ATCC 12202 | dispersed throughout, said string culture inoculum having a sufficient number of stabilized cells adhered thereto to produce at least $10^5$ cells per milliliter upon incubation in 3 milliliters of suitable broth at 37° C for 2 hours. The string culture inocula of the present invention are useful as quality control cultures for positive as well as negative controls in clinical bacteriology procedures and drug susceptibility testing.

8 Claims, No Drawings

STRING CULTURE INOCULUM

The present invention encompasses a method for preparing a standardized culture inoculum of an organism selected from the group consisting of:

| | |
|---|---|
| Salmonella typhimurium | ATCC 6994 |
| Klebsiella pneumoniae | ATCC 10031 |
| Enterobacter cloacae | ATCC 11367 |
| Escherichia coli | ATCC 25922 |
| Citrobacter freundii | ATCC 6750 |
| Proteus vulgaris | ATCC 881 |
| Pseudomonas aeruginosa | ATCC 15442 |
| Shigella sonnei | ATCC 11060 |
| Serratia marcescens | ATCC 14756 |
| Staphylococcus aureus | ATCC 25923 |
| Staphylococcus eipidermidis | ATCC 17917 |
| Streptococcus faecalis | ATCC 10541 or |
| Streptococcus pyogenes | ATCC 12202 | comprising soaking a sterilized string in a stabilized cell concentrate of one of said organisms and then desiccating the string to dryness, said stabilized cell concentrate having $10^8 - 10^{10}$ cells per milliliter, said standardized culture inoculum having sufficient stabilized cells adhered therein to produce at least $10^5$ cells per milliliter upon incubation in 3 milliliters of trypticase soy broth at 37° C for 2 hours. The present invention also encompasses the string culture inocula produced by the aforementioned method. The string culture inocula of the present invention provide at least $10^5$ cells per milliliter upon incubation in 3 milliliters of trypticase soy broth after storage at refrigerated temperatures for 6 months or more.

The present invention encompasses a sterilized string of cotton, wool, or synthetic fibers, or combinations thereof or pieces of cloth made of such fibers on which stabilized cells of the above indicated organisms are placed. The pieces of string are a standard length of about ¼ to 1 ½ inches in length; preferably 1 inch lengths of cotton twine are used. Thus, a stabilized cell concentrate is prepared by conventional techniques of growing cells in a suitable media, centriguging and isolating the cells. These cells are then suspended in a suitable stabilizer such as a nutrient gelatin or Marshall and Scott's stabilizer. A variety of techniques for growing and stabilizing cell concentrates are known in the microbiological arts, Bauer, et al. *Clinical Laboratory Methods*, C. V. Mosby Co. 1974, Chapt. 16.

Those skilled in microbiological arts will recognize the interchangeability of such techniques. For purposes of the present invention it is required that the stabilized cell concentrate have $10^8 - 10^{10}$ cells per milliliter so that a sufficient number of cells will be adhered to the string. Although the exact number of cells adhered to the string is not determined, the requisite number of cells adhered is defined by number of cells which can be grown in 3 milliliters of trypticase soy broth at 37° C for 2 hours. The standardized culture inoculum of the present invention has sufficient number of stabilized cells adhered thereto to provide at least $10^5$ cells per milliliter after storage for 6 months or more upon incubation in 3 milliliters of suitable broth at 37° C for 2 hours. String culture inocula of the present invention produce at least $10^5$ cell per milliliter upon incubation in 3 milliliters of trypticase soy broth (TSB) at 37° C for 2 hours.

In a preferred embodiment of the present invention 1 inch segments of cotton twine are soaked for 30 minutes in a stabilized cell concentrate having $10^8 - 10^{10}$ cells per milliliter of one of:

| | |
|---|---|
| Salmonella typhimurium * | ATCC 6994 |
| Klebsiella pneumoniae | ATCC 10031 |
| Enterobacter cloacae | ATCC 11367 |
| Escherichia coli | ATCC 25922 |
| Citrobacter freundii | ATCC 6750 |
| Proteus vulgaris | ATCC 881 |
| Pseudomonas aeruginosa | ATCC 15442 |
| Shigella sonnei | ATCC 11060 |
| Serratia marcescens | ATCC 14756 |
| Staphylococcus aureus | ATCC 25923 |
| Staphylococcus epidermidis | ATCC 17917 |
| Streptococcus faecalis | ATCC 10541 or |
| Streptococcus pyogenes | ATCC 12202. |

* ATCC cultures are available to the public from American Type Culture Collection, 12301 Parklawn Drive, Mockville, Maryland 20852

The strings having cells adhered thereto are then desiccated to dryness. This process provides a string culture inoculum which has a sufficient number of stabilized cells adhered thereto so that incubation in 3 milliliters of typticase soy broth (TSB) at 37° C for 2 hours provides at least $10^5$ cells per milliliter.

Media formulation, sterilization techniques, and identification are set out in many standard microbiological references:

*Diagnostic Procedures*, Bodily et al. 5th ed. American Public Health Association, Inc. (1970), pages 791–876; *Clinical Laboratory Methods*, Bauer et al, 8th ed. 1974, Chap. 16; and *Methods in Clinical Bacteriology*, D. Branson, Charles C. Thomas, Springfield, Ill.

The need for quality control programs in clinical laboratories is well recognized, Burry and Teeney, Amer. J. Med. Technol. 33, (1967) 387–393, A. R. Fodor, Health Lab Sci. 5, 5–11 (1968). Until recently these programs depended upon the maintenance of stock cultures obtained from clinical specimens, purchased from commercial sources, or obtained from another laboratory. Solid media transfer and lyophilization have inherent disadvantages of mutation and/or contamination. Lyophilization is expensive and time consuming. Dehydrated discs have been used as inocula for control cultures. These discs are thin and difficult to use in that they tend to crumble upon handling with a forcep.

String culture inocula of the present invention are advantageous in that they are easy to handle with a sterile forcep. Unexpectedly it has been found that some of the aforementioned organisms can be stored on string for 3 years or more. It is unexpected that all the indicated organisms would be stable on a string for more than 1 year since generally these organisms are not viable on dry surfaces and, in fact, the art generally teaches the necessity of a protective agar coating or expensive and time consuming lyophilization.

The utility of the string culture inocula of the present invention is illustrated in Table I wherein the organisms are used as potitive and negative media controls with standard media and methods set out in *Diagnostic Procedures*, Bodily et al. 5th ed. America Public Health Association, Inc. (1970) pages 791–876; *Clinical Laboratory Methods*, Bauer et al. 8th ed. 1974, chap. 16; and *Methods in Clinical Bacteriology*, D. Branson, Charles C. Thomas, publisher, Springfield, Ill.

TABLE I

| Medium | Positive control | Negative control |
|---|---|---|
| Blood agar, sheep | S. pyogenes | O |
| Hektoen Enteric agar | Mixture of Salmonella and (Shigella) | E. coli |
| MacConkey agar | Mixture of E. coli and (Shigella) | S. Epidermidis |
| Trypticase soy agar | S. epidermidis | O |
| Carbohydrates, phenol red broth base | | |
| Adonitol | (Klebsiella) | P. aeruginosa |
| Dulcitol | Salmonella | P. aeruginosa |
| Inositol | (Klebsiella) | P. aeruginosa |
| Maltose | E. coli | P. aeruginosa |
| All other | E. cloacae | P. aeruginosa |
| Citrate, Simmon's | E. cloacae | E. coli |
| Decarboxylases | E. coli and E. cloacae | P. vulgaris |
| Enterococcal media (bile-esculin, SE agar, etc.) | (Enterococcus) | S. pyogenes |
| Gelatin | P. vulgaris | E. coli |
| KCN broth | E. cloacae | E. coli |
| Lysine iron agar | Salmonella/P. vulgaris | E. cloacae |
| Motility | E. coli | S. epidermidis |
| MR-VP broth | E. coli/E. cloacae | E. coli/E. cloacae |
| Nitrate agar or broth | coliE. coli | S. pyogenes |
| Phenylalanine agar | P. vulgaris | E. coli |
| Selenite broth | Salmonella | E. coli |
| SIM | E. coli / Salmonella | E. cloacae for H₂S and I or (Shigella) for all |
| Todd Hewitt broth | S. pyogenes | O |
| Triple sugar iron agar | Salmonella/E. coli | P. aeruginosa |
| Trypticase soy broth | S. epidermidis | O |
| Urea agar (Christensen) | P. vulgaris/E. cloacae | E. coli |
| XLD (xylose lysine, deoxycholate) | | Citrobacter freundii ATCC 6750 |

Table II illustrates reagent and stain control.

TABLE II

| Reagent | Positive control | Negative control |
|---|---|---|
| Bacitracin discs | S. pyogenes | (Alpha - hemolytic streptococcus) |
| Catalase | S. faecalis | |
| Coagulase plasma | S. aureus | S. epidermidis |
| Ferric chloride, 10% | P. vulgaris | E. coli |
| Hydrogen peroxide, 3% | S. Aureus | S. pyogenes |
| Kovac's | E. coli | E. cloacae |
| Nitrate reagents | E. coli | S. pyogenes |
| Oxidase reagent | P. aeruginosa | E. coli |
| Gram stain | S. aureus | E. coli |

E. coli ATCC 25922 and *Staphylococcus aureus* ATCC 25923 are used as standard isolates for drug susceptibility testing via the Kirby-Bauer procedure, Federal Register 36, April 10, 1971, at page 6901, Hospital Practice 5, 91, 1970, and American J. Clin. Path. 45 493–496(1966).

The following examples are illustrative of the present invention and are not intended to limit the invention in spirit or scope.

EXAMPLE 1

Under aseptic conditions E. coli ATCC 25922 stock culture maintained at −15° C in 5% glycerine or 5% dimethyl sulfoxide is thawed and inoculated into an Erlenmeyer flask containing 40 milliliters of trypticase soy broth (TSB), an all-purpose medium made from pancreatic digest of casein and soybean peptone. The flask is then incubated for about 24 hours at 37° C. 10 milliliters of this growth is placed in a 2-liter Erlenmeyer flask containing 1000 ml of TSB and incubated 18 hours at 37° C. The growth from the flask is harvested at the mid-log phase by centrifugation at 2000 rpm for 20 minutes. The harvested growth is suspended in 50 milliliters of nutrient gelatin stabilizer which contains 3 grams beef extract, 5 grams peptone, and 120 grams of gelatin per liter of deionized water. The medium is dissolved by boiling, 0.5% sodium chloride is added and the pH is adjusted to 7.6 and autoclaved at 121° C for 15 minutes. Then filter-sterilized L-ascorbic acid is added in concentration of 0.25% which brings down the final pH of the stabilizer to 7.2. This stabilized cell suspension has $10^8 - 10^{11}$ cells per milliliter as determined by the most probable number (MPN) method. This growth is emulsified by bubbling air through a sterile cotton plugged pipette. 25 milliliters of this suspension is poured into a sterile petri dish containing 60, 1-inch long, sterilized lengths of cotton string (51 pounds, Shuford Mills, Inc. Hickory, S.C.). The strings are allowed to soak for one half hour, they are placed in a sterile vial which contains 2 heat treated ¼ g silica gel packets and desiccated at 150 mm of Hg for 24 hours. The vials are sealed and stored at 4° C. A string culture inoculum incubated in 3 ml of TSB for two hours provides more than $10^5$ cells per milliliter.

EXAMPLE 2

Following the procedure set out in Example 1 and replacing E. coli ATCC 25922 with *Proteus vulgaris* ATCC 881 provides a string culture inoculum of the latter organism.

EXAMPLE 3

Following the procedure set out in Example 1 and replacing E. coli ATCC 25922 with *Salmonella typhimurium* ATCC 6994 provides a string culture inoculum of the latter organism.

EXAMPLE 4

Following the procedure set out in Example 1 and replacing E. coli ATCC 25922 with *Klebsiella pneumoniae* ATCC 10031 provides a string culture inoculum of the latter organism.

EXAMPLE 5

Following the procedure set out in Example 1 and replacing E. coli ATCC 25922 with *Enterobacter cloacae* ATCC 11367 provides a string culture inoculum of the latter organism.

EXAMPLE 6

Following the procedure set out in Example 1 and replacing E. coli ATCC 25922 with *Citrobacter freundii* ATCC 6750 provides a string culture inoculum of the latter organism.

EXAMPLE 7

Following the procedure set out in Example 1 and replacing *E. coli* ATCC 25922 with *Pseudomonas aeruginosa* ATCC 15442 provides a string culture inoculum of the latter organism.

EXAMPLE 8

Following the procedure set out in Example 1 and replacing *E. coli* ATCC 25922 with *Shigella sonnei* ATCC 11060 provides a string culture inoculum of the latter organism.

EXAMPLE 9

Following the procedure set out in Example 1 and replacing *E. coli* ATCC 25922 with *Serratia marcescens* ATCC 14756 provides a string culture inoculum of the latter organism.

EXAMPLE 10

Following the procedure set out in Example 1 and replacing *E. coli* ATCC 25922 with *Staphylococcus aureus* ATCC 25923 provides a string culture inoculum of the latter organism.

EXAMPLE 11

Follwoing the procedure set out in Example 1 and replacing *E. coli* ATCC 25922 with *Streptococcus faecalis* ATCC 10541 provides a string culture inoculum of the latter organism.

EXAMPLE 12

Following essentially the procedure set out in Example 1 and replacing *E. coli* ATCC 25922 with *Streptococcus pyogenes* ATCC 12202 provides a string culture inoculum of the latter organism. With this organism the growth medium is fortified with 5% sterile sheep blood and plates are incubated in a candle jar in order to increase the concentration of carbon dioxide in the incubation atmosphere.

EXAMPLE 13

The procedure of Example 1 is repeated using 50 ml of Marshall and Scott's stabilizer (pH 7.0) which is 0.15 molar in sucrose, 0.2 molar in sodium glutamate, and 0.02 molar in semicarbazide all 3 sterilized with 0.22 molar millipore filter in place of nutrient gelatin.

EXAMPLE 14

The procedure of Example 1 is repeated using 50 ml of Marshall and Scott's stabilizer which is 0.15 molar in sucrose, 0.2 molar in sodium glutamate, and 0.03 molar in semicarbazide in place of nutrient gelatin.

What is claimed is:

1. A method for preparing a standardized culture inoculum of an organism selected from the group consisting of

| | |
|---|---|
| *Salmonella typhimurium* | ATCC 6994 |
| *Klebsiella pneumoniae* | ATCC 10031 |
| *Enterobacter cloacae* | ATCC 11367 |
| *Escherichia coli* | ATCC 25922 |
| *Citrobacter freundii* | ATCC 6750 |
| *Proteus vulgaris* | ATCC 881 |
| *Pseudomonas aeruginosa* | ATCC 15442 |
| *Shigella sonnei* | ATCC 11060 |
| *Serratia marcescens* | ATCC 14756 |
| *Staphylococcus aureus* | ATCC 25923 |
| *Staphylococcus epidermidis* | ATCC 17917 |
| Streptococcus faecalis | ATTC 10541 |
| | or |
| *Streptococcus pyogenes* | ATCC 12202 | comprising soaking a sterilized string in a stabilized cell concentrate of one of said organisms and then desiccating the string to dryness, said stabilized cell concentrate having $10^8 - 10^{10}$ cells per milliliter, said standardized culture inoculum having sufficient stabilized cells adhered thereto to produce at least $10^5$ cells per milliliter upon incubation in 3 milliliters of trypticase soy broth at 37° C. for 2 hours.

2. The method of claim 1 wherein the string is a ¼ – 1½ inch segment of cotton twine.

3. The method of claim 1 wherein the cells are stabilized with nutrient gelatin stabilizer.

4. The method of claim 1 wherein the cells are stabilized in media 0.15 molar in sucrose, 0.2 molar in sodium glutamate, and 0.02 to 0.03 molar in semicarbazide.

5. A string culture inoculum comprising a string having dried stabilized cells of one of

| | |
|---|---|
| *Salmonella typhimurium* | ATCC 6994 |
| *Klebsiella pneumoniae* | ATCC 10031 |
| *Enterobacter cloacae* | ATCC 11367 |
| *Escherichia coli* | ATCC 25922 |
| *Citrobacter freundii* | ATCC 6750 |
| *Proteus vulgaris* | ATCC 881 |
| *Pseudomonas aeruginosa* | ATCC 15442 |
| *Shigella sonnei* | ATCC 11060 |
| *Serratia marcescens* | ATCC 14756 |
| *Staphylococcus aureus* | ATCC 25923 |
| *Staphylococcus eipidermidis* | ATCC 17917 |
| *Streptococcus faecalis* | ATCC 10541 or |
| *Streptococcus pyogenes* | ATCC 12202 | dispersed throughout, said string culture inoculum having a sufficient number of stabilized cells of said organism adhered thereto to produce at least $10^5$ cells per milliliter upon incubation in 3 milliliters of trypticase soy broth at 37° C. for 2 hours.

6. The string culture inoculum of claim 5 wherein the organism is stabilized on a ¼ to 1½ inch segment of cotton twine.

7. The string culture inoculum of claim 5 wherein the organism is stabilized with nutrient gelatin stabilizer.

8. The string culture inoculum of claim 5 wherein the organism is stabilized in media 0.15 molar in sucrose, 0.2 molar in sodium glutamate, and 0.02 to 0.03 molar in semi-carbazide.

* * * * *